United States Patent [19]

Raemer et al.

[11] Patent Number: 5,005,572
[45] Date of Patent: Apr. 9, 1991

[54] $CO_2$ INDICATOR AND THE USE THEREOF TO EVALUATE PLACEMENT OF TRACHEAL TUBES

[75] Inventors: Daniel B. Raemer, Brookline; David R. Walt, Lexington; Christianne Munkholm, Salem, all of Mass.

[73] Assignee: Brigham & Women's Hospital, Boston, Mass.

[21] Appl. No.: 303,952

[22] Filed: Jan. 31, 1989

Related U.S. Application Data

[63] Continuation of Ser. No. 161,046, Feb. 26, 1988, abandoned.

[51] Int. Cl.[5] .............................................. A61M 16/00
[52] U.S. Cl. ............................. 128/207.14; 128/205.23
[58] Field of Search ............... 128/207.14, 768, 205.23; 422/58, 91, 55; 436/133

[56] References Cited

U.S. PATENT DOCUMENTS

| | | | |
|---|---|---|---|
| 3,068,073 | 12/1962 | Stanford | 436/133 |
| 3,373,735 | 3/1968 | Gallagher | 128/768 |
| 3,694,164 | 9/1972 | Guenther | 422/58 |
| 3,754,867 | 8/1973 | Guenther | 422/91 |
| 4,557,900 | 12/1985 | Heitzmann | 422/55 |
| 4,691,701 | 9/1987 | Williams | 128/207.14 |
| 4,728,499 | 3/1988 | Fehder | 128/207.14 |
| 4,734,125 | 3/1988 | Gehring et al. | 548/375 |

OTHER PUBLICATIONS

Jeffrey A. B., et al., *Anesthesiology*, 60:613-614 (1984).

Primary Examiner—Edgar S. Burr
Assistant Examiner—Aaron J. Lewis
Attorney, Agent, or Firm—Sterne, Kessler, Goldstein & Fox

[57] ABSTRACT

The invention relates to a $CO_2$ detector for the detection of $CO_2$ in respiratory gases. In particular, the invention relates to medical devices which contain a $CO_2$ detector disposed within the devices to allow detection of $CO_2$ within respiratory gases.

The invention also relates to a method for determining the proper placement of an intubation device comprising inserting a tracheal tube having a $CO_2$ detector disposed within, and observing whether the $CO_2$ detector changes color in response to the $CO_2$ which is present in respiratory gases.

The $CO_2$ detectors of the invention comprise a pH sensitive dye and a solid phase support. The $CO_2$ detectors of the invention may further comprise a phase transport enhancer which allows the $CO_2$ detector to respond contemporaneously with the presence or absence of $CO_2$ in a respiratory gas on a breath by breath basis.

8 Claims, 4 Drawing Sheets

$CO_2$ INDICATOR AND THE USE THEREOF TO EVALUATE PLACEMENT OF TRACHEAL TUBES

This application is a continuation of application Ser. No. 161,046, filed Feb. 26, 1988, abandoned.

BACKGROUND OF THE INVENTION

1. Field of the Invention

This invention relates generally to medical devices, and more particularly to a detection device for determining whether a tracheal tube is properly positioned within the trachea of a patient.

2. Description of Related Art

There are a number of methods used by anesthesiologists to confirm that a tracheal tube has been properly positioned within the trachea of a patient. While anesthesiologists take great care to make certain that intubation of the esophagus does not occur, it is often difficult to know contemporaneously with insertion of the endotracheal device whether the device has unintentionally been placed in the esophagus. Undiagnosed intubation of the esophagus leads, in some cases, to death of the patient. It is therefore critical that there be a simple and accurate method of determining whether a tracheal tube has been properly positioned within the trachea of a patient.

In addition to the importance of proper placement of a tracheal tube, one problem which is encountered by anesthesiologists and others is the question of whether a patient is breathing. A device which confirms both proper placement of a tracheal tube and breathing would provide a much needed tool for use by the medical community.

One device which attempts to address the tracheal tube placement problem is described in "The Einstein Carbon Dioxide Detector," 60 *Anesthesiology* 613 (1983). In this article, a device is described which recognizes the well established fact that gases expelled from the trachea contain $CO_2$ while gases within the esophagus do not.

The operation of the Einstein detector device is broadly based upon a visual indication of the carbon dioxide concentration found in expired gases. The technique described in the *Anesthesiology* article is based on the fact that gases expired from the lungs contain between 4% and 6% $CO_2$ whereas atmospheric air, which is expelled from the esophagus, has a negligible amount of $CO_2$. The device utilizes an adapter connected at one end to a mucous trap. A tube connected to the trap is filled with a liquid indicator solution, and the catheter end of the trap is positioned to be well below the indicator fluid level. The adapter is attached to the endotracheal tube, and expired gases are pumped through the indicator solution and are allowed to bubble therethrough. Utilizing a cresol red and phenolphthalein solution, a gradual color change from red to yellow occurs after several seconds upon proper tracheal intubation. No color change of the solution suggests esophageal intubation.

The Einstein detector has many drawbacks. Because the gas is bubbled through a liquid indicator, expired gas must be pumped through the liquid. This, of course, requires additional equipment not usually associated with a conventional tracheal tube, such as a conduit or sample tube, a mucous trap, and of course, the liquid chemicals themselves. Liquid chemicals have their own inherent disadvantages; in particular, they are impractical because they can spill. Further, the change in color does not occur until three to five seconds after trap chamber. The Einstein $CO_2$ detector also does not follow the breathing pattern of the patient. In other words, the indicator used by the Einstein $CO_2$ detector is not reversible on a time frame which would enable visual confirmation of breathing. Thus, the Einstein $CO_2$ detector is limited in its ability to provide an indication of proper or improper intubation. It does not actively detect breathing; it only detects placement.

There are, of course, a number of different types of detectors associated with intubation devices which are used in varying applications. For example, U.S. Pat. No. 3,373,735 to Gallagher, teaches a device which indicates proper placement of a tube into a patient's stomach. After the tube is inserted into the stomach of a patient, a small amount of the stomach fluid is drawn into the tube to wet a color-change indicator. When the tube is properly inserted within the stomach of a patient, the indicator will turn red. If, however, the end of the tube has been improperly placed into the lungs, the indicator would remain a blue color. This device, of course, has nothing to do with the detection of respiration.

In addition to the Einstein $CO_2$ detector, there are other carbon dioxide detectors for both medical and nonmedical applications. In the medical area, infrared and mass spectroscopy are used as $CO_2$ detectors. In the non-medical area, U.S. Pat. No. 3,694,164 to Guenther discloses a system for sensing the carbon dioxide content of a gas. One embodiment taught by Guenther utilizes an infrared source which is mounted a fixed distance from a cell constructed on a conductive material such as aluminum. Radiation from the infrared source is focused onto the face of the cell and covers a major portion of the face of the cell. The face of the cell contains a small aperture which is sealed by a window which transmits virtually 100% of the infrared radiation which is absorbed by pure $CO_2$ which fills the cell. Both the inner chamber of the cell and the face of the cell are fitted with thermistors which are connected to a sensing device for detecting the differences between the temperatures of the two thermistors. The source and sensor are turned on and allowed to come to temperature equilibrium in an atmosphere virtually free of $CO_2$, and the sensor is set to a chosen reference. Upon exposure to an atmosphere of $CO_2$ gas, the radiation formerly absorbed by the gas in the cell is decreased, whereas that radiation absorbed by the face of the cell is affected only slightly. The temperature differential allows the user to detect the content of carbon dioxide in the cell. While this device detects $CO_2$, it is not colorometric, it is not rapid and is not positioned in a gas stream.

In another embodiment shown in the Guenther patent, a porous impregnated surface contains a color-change indicator which changes in accordance with the carbon dioxide content. This embodiment, however, does not discuss the ability of the device to cycle from one color to another at a rate which is on the same order of magnitude as is the rate of breathing. In general, Guenther is not directed toward providing a $CO_2$ detector for use as a medical device.

U.S. Pat. No. 3,068,073 to Stanford discloses a device for detecting the presence and determining the content of carbon dioxide in gases. The gas containing an undetermined amount of carbon dioxide is passed through a solid reagent which includes alumina carrying parent container and changes color by contact with carbon dioxide. The quantity of carbon dioxide is determined by the length of time it takes for the color indicator to change the colors. In medical applications such as determining whether the intubation of the trachea has occurred, a rapid time change is preferred. Thus, such a time-consuming procedure would not be appropriate for medical applications.

It is therefore one object of the invention to provide a $CO_2$ indicator which is contained within the respired gas stream of a tracheal tube.

It is a further object of the invention to provide a tracheal tube having a colorimetric $CO_2$ detector which follows the breathing pattern of a patient.

SUMMARY OF THE INVENTION

In accordance with the purposes of the present invention as embodied and described herein, the present invention is an intubation apparatus which includes a tube for receiving expiration gas. Within the tube is a detector for visually indicating whether a predetermined threshold concentration of carbon dioxide is present within the tube. In one aspect of the invention the detector is made up of indicator material which changes from one color to another and back to the first color in response to the presence then absence of a predetermined amount of $CO_2$ gas. In yet another aspect of the invention the indicator material includes a solid phase support and a pH sensitive dye. The dye may be adsorbed onto, covalently attached to, or entrapped within the solid phase support. To improve and enhance the response of the dye, a mixture of the pH sensitive dye and a phase transport enhancer is added to the solid phase support.

In yet another aspect of the invention, the detector may further contain a thin membrane disposed over the detector.

The invention also relates to methods for determining the proper placement of a tracheal intubation device comprising inserting a device comprising (a) an endotracheal apparatus which includes a tracheal tube defining a gas path; and (b) a $CO_2$ detector disposed within said tracheal apparatus at a location which is in the gas path of said tube and is visible when said endotracheal tube is inserted, said detector being capable of indicating whether a substantial concentration of $CO_2$ is present in said gas; and observing a color change of the indicator which indicates the presence of $CO_2$ in the respiratory gas and thereby the proper placement of the endotracheal tube.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION OF THE PREFERRED EMBODIMENTS

Figure 1:
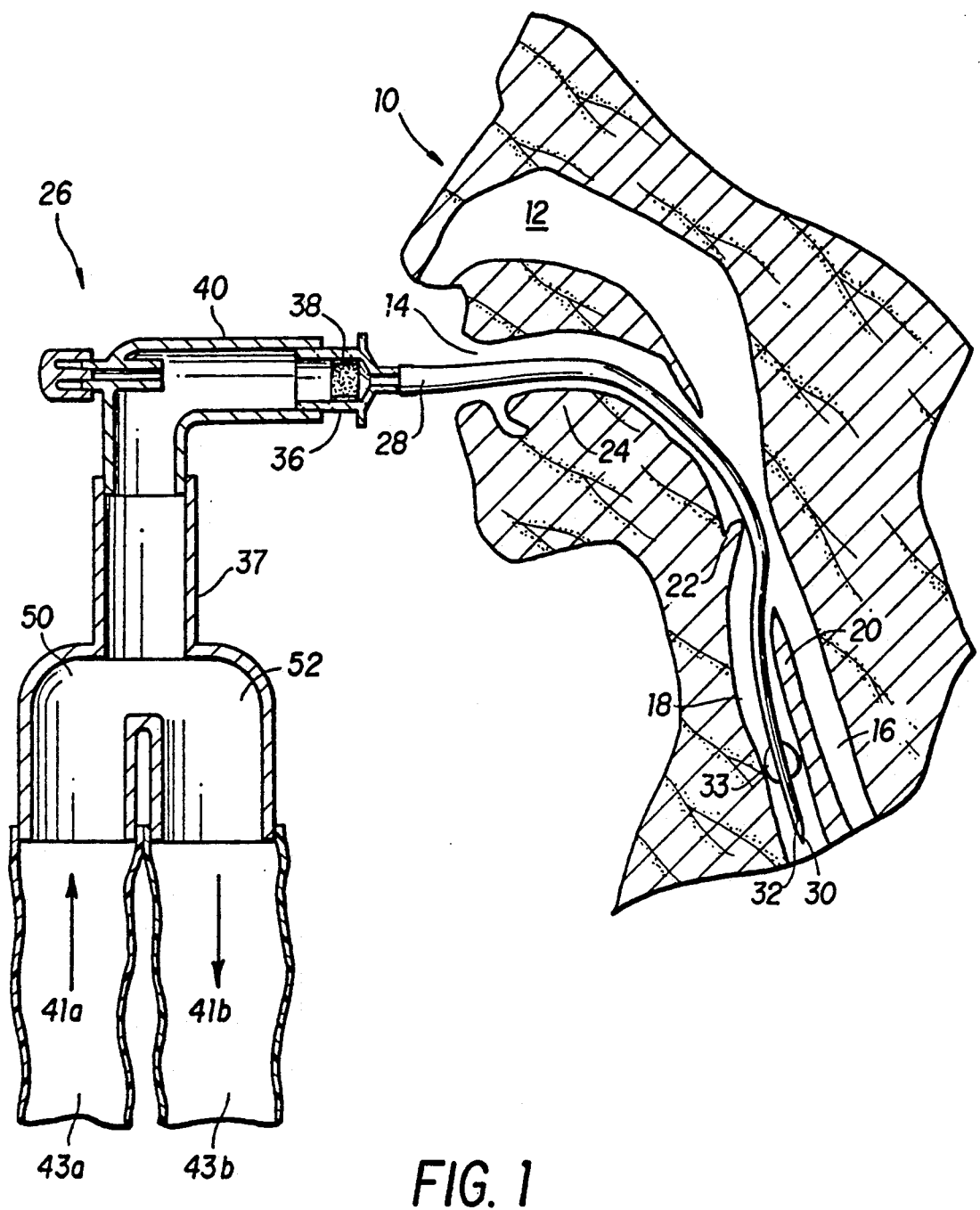
FIG. 1 is a schematic illustration (not to scale) of a patient and of an intubation device according to the invention.

The present invention comprises a device for detecting whether a tracheal tube is properly positioned within the trachea. To assist in its understanding, a brief description of the anatomy may be helpful. FIG. 1 illustrates a schematic (not to scale) representation of a patient designated generally as 10, and of an endotracheal apparatus 26 using the present invention. Normally, air is inhaled into the lungs of a patient 10 via either the nasal cavity 12 or the mouth 14. Similarly, $CO_2$ gas expired from the lungs is exhaled through the nasal cavity or the mouth. The esophagus 16, which is oblong in cross section, connects the mouth with the stomach and provides a tube for ingestion of foods and liquids. The trachea 18 is positioned in front of the esophagus 16 as shown in FIG. 1 and connects the mouth and nasal cavity with the lungs. The esophagus 16 and the trachea 18 are separated by a dividing wall 20, the corniculate. The epiglottis 22 is a thin membrane of cartilage which is positioned behind the tongue 24 in front of the opening of the larynx (not shown). Forming the lower and back part of the cavity of the larynx is a ring-shaped piece of cartilage known as the cricoid membrane (not shown).

A typical respiration or breathing circuit which will hereinafter be referred to as the "endotracheal apparatus" is shown generally as 26. The endotracheal apparatus 26 is made up of a number of component parts connector 40 and a bifurcation unit 37.

The tube 28 has an angled open end 30 which provides for easy insertion into the trachea of a patient 10 through either the mouth 14, the nasal cavity 12 or through a cricoid membrane puncture (not shown). Formed in the wall of tube 28 near the angled end 30 is a second opening 32. Also positioned near the angled end 30 adjacent the second opening 32 is a cuff 33 made of a thin plastic material which may be inflated to contact the sides of the tracheal wall.

In the endotracheal apparatus shown in FIG. 1, the tube 28 is attached to the adapter 36 which in turn is attached to the elbow connector 40. The bifurcation unit 37 provides a gas inhalation path 50 and a gas exhalation path 52. The direction of gas flow is shown by the arrows labeled 41a and 41b. Attached to the inhalation path 50 and exhalation path 52 are a first flexible tube 43a and a second flexible tube 43b, respectively.

Tracheal tube 28 has a centrally located primary passage for allowing oxygen and other gases to be passed into the lungs. A conventional secondary passage (not shown) connecting cuff 33 to a syringe may also be provided to allow inflation of the cuff 33. This enables the cuff 33 to contact the inside of the trachea 18, thereby preventing gases from escaping through the mouth and nose of the patient.

The present invention provides a device, such as a detector 38, which enables the user to determine whether the endotracheal tube 28 is properly placed in the trachea 18. Detector 38, in a preferred embodiment, is located in adapter 36 and includes means that respond to a minimum concentration of carbon dioxide. The response preferably takes the form of a visually observable state change, such as changing from one color to another. The principle of operation is based on the fact that gas expired from the lungs has a high concentration of $CO_2$ while gas which is inspired, driven to the stomach and returned through the esophagus has an extremely low concentration of $CO_2$. By placing the detector 38 contiguous with gases expired from patient 10, it is possible to chemically determine if the concentration of carbon dioxide in gas expired through the endotracheal tube exceeds a minimum accepted value. If it does, the detector, which includes a pH sensitive dye, will change from one color to another thus visually indicating to the attending physician or other personnel the presence of $CO_2$. This in turn means that the endotracheal tube is properly positioned within the trachea rather than the esophagus. The detector 38 may also cycle between one color and another in response to breathing, i.e., on a breath-by-breath basis.

To accomplish these goals a detector 38 is provided in the endotracheal apparatus 26 and is positioned so that gases expired from the patient 10 will make contact with the detector 38. The detector 38 may be installed at various places in the respiratory gas path. Although in a preferred embodiment of the invention the detector 38 is positioned on the inside wall of the adapter 36, it may also be located in the portion of the tube 28 which is not within patient 10, the elbow adapter 40, the bifurcation unit 37 or at a location even further downstream. It is preferred, however, that the detector be located as close to the source of exhalation gas as possible. Naturally, the detector 38 must be seen by an observer or operatively connected to a device which may be read by an observer. In a preferred embodiment of the invention, the part of the endotrachael apparatus 26 housing the detector 38 is made of a transparent material so that the detector 38 can be seen by an observer.

The detector 38 includes a solid indicator material which alleviates the problems associated with a liquid indicator and enables the detector 38 to be positioned in a conventional endotracheal apparatus without having to pump expiration gases through a liquid.

Several indicator materials and accessory materials have been found for use in the detector 38 which change color in a time frame which corresponds to that of inhalation and exhalation of the patient 10. This is a major advantage in that it enables breath by breath detection of both proper intubation and breathing.

Having stated this, it is worth noting that there may be applications where a fast response time is not necessary. If this is the case, alternative indicator materials may be incorporated into the invention which are tailored to the particular application without deviating from the spirit of the invention.

Figure 2:
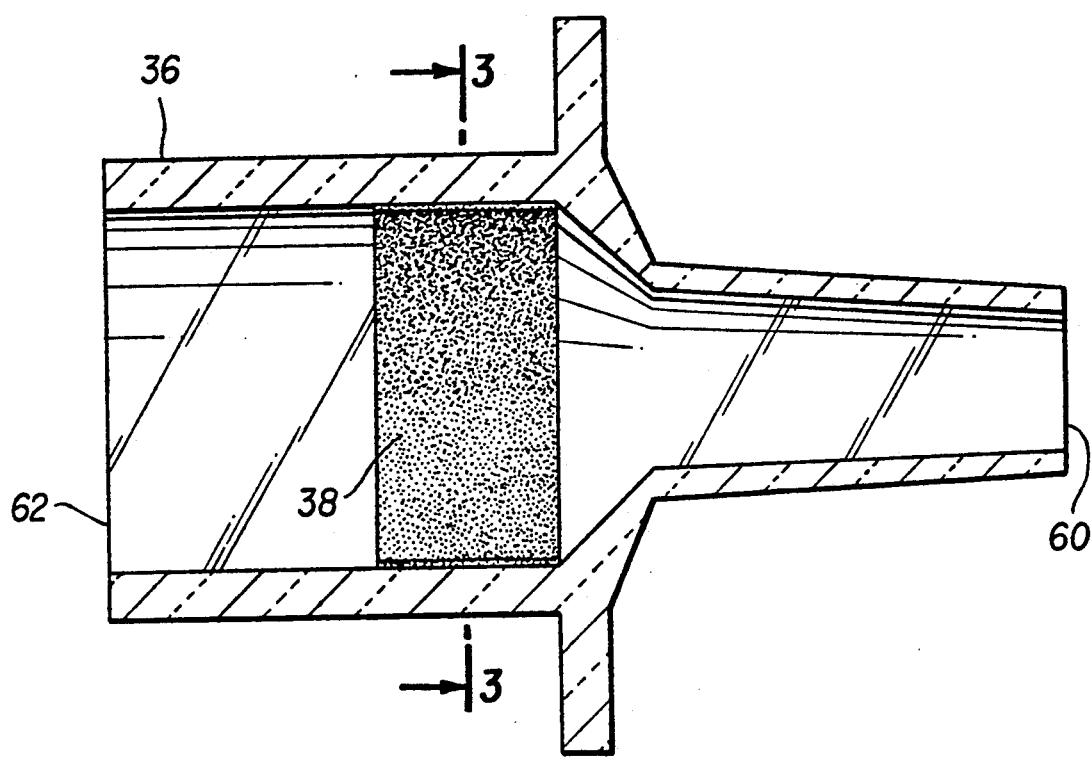
FIG. 2 is a section view of an adapter and detector element of the invention.
Figure 3:
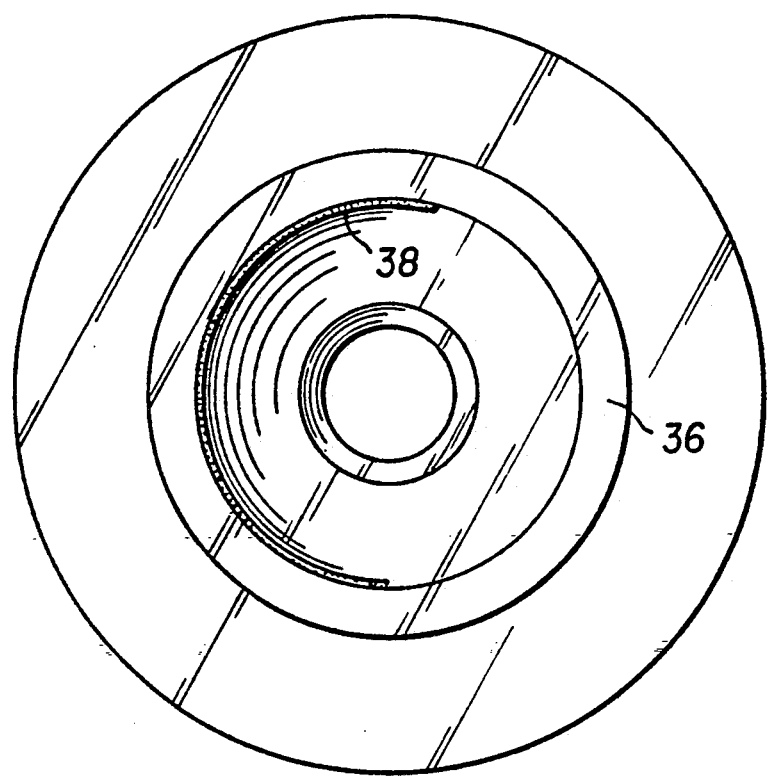
FIG. 3 is a cross-sectional view of the adapter and detector cut along line 3—3 of FIG. 2.

FIG. 2 is an enlarged view of adapter 36 shown in FIG. 1 while FIG. 3 is a cross-section of FIG. 2. This adapter has a first end 60 which is adapted to be connected to tube 28. The adapter 36 also has a second end 62 which is typically of larger diameter than the first end. This second end 62 is adapted to be connected to the L-shaped connector 40. The precise configurations of the adapter 36 and the other components of the endotracheal tube are not particularly important to the present invention. What is important is that the detector 38 is positioned in the normal stream of exhaled gases and is visible to an observer. The detector 38 can be made of a number of different materials as will be discussed later. As seen in FIG. 3, the detector 38 may follow the curve of adaptor 28 thereby not affecting the flow of gases through adapter 28.

Figure 4:
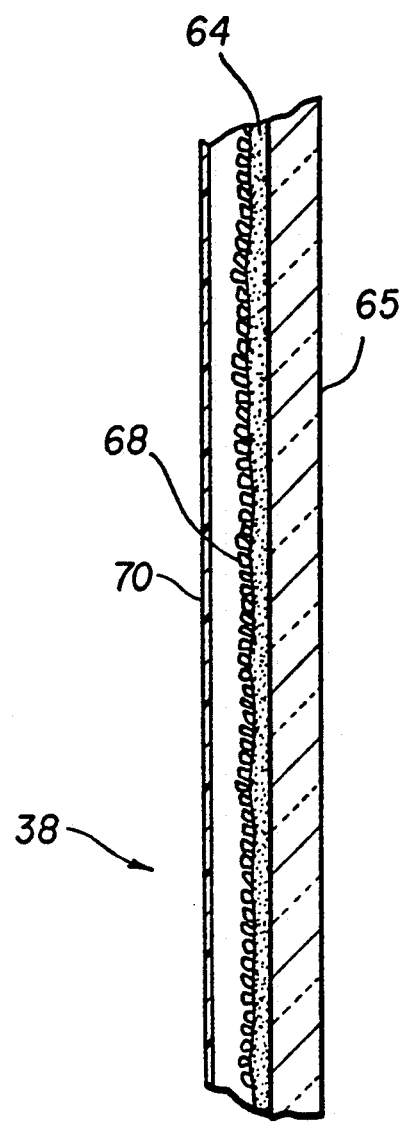
FIG. 4 is a schematic view showing one embodiment of how the indicator and support material of the invention is attached to a backing.

FIG. 4 shows a cross section schematic view of the detector 38. In this figure, the detector is shown to be flat. In a preferred embodiment, however, the detector conforms to the shape of the inner wall of adapter 36 as mentioned above. A thin layer of adhesive 64 is applied to a backing member 65 such as a strip of transparent polymeric sheet. Indicator material 68 is liberally sprinkled onto the adhesive, the excess is removed and the system is left to dry. The detector 38 having indicator material 68 is then inserted into the adapter 36 so that gas passing through adapter 36 will be contiguous with the indicator material 68. The indicator material 68 includes a support material such as a porous glass and a pH sensitive dye which will change colors when in contact with $CO_2$.

Various backings in various shapes and sizes may be used to practice the invention. The material, size, shape, and physical properties of the backing structure are not critical to the device's operation. By constructing the adapter 36 itself out of a material such as a controlled pore glass (CPG) tube, the need for a separate, independent backing member or a separate support material may be eliminated.

The attachment of the support material and indicator to the backing may be accomplished with various glues and adhesives which include, but are not limited to, epoxy, cyanoacrylate, silicone rubber, and tape. Any glue or adhesive which does not interfere adversely with the indicator may be used to practice the invention. If the porous support is made into a plate or tape of the appropriate dimensions, no glue or adhesive may be required.

In one embodiment of the invention, the detector 38 is covered with a thin polymeric membrane 70 as shown in FIG. 4. By covering the detector 38 with a hydrophobic polymeric membrane 70, the detector material may be protected from undesirable sources of contamination such as water, stomach acids, mucus, and other undesirable liquids. Such specificity may be achieved by selecting a polymeric membrane which exclusively passes gasses but not liquid. By selecting a membrane with such a characteristic, a high degree of selectivity can be achieved by using a sensitive but otherwise unselective indicator material 68.

A preferred polymeric membrane is polytetrafluoroethylene (PTFE) membrane, also known as Gortex, which freely allows the passage of $CO_2$ through the membrane, but does not allow liquid water to pass. Such a Gortex membrane may have a pore size of 1 or 3 $\mu M$ or any other suitable size. Other suitable membranes may be selected by one of ordinary skill in the art which allow $CO_2$ to pass without undue experimentation.

In another embodiment of the invention, layered chemistry is used to form the detector 38. Here, layers of polymer bound chemistry are prepared to tailor the response to the system. For instance, a selective membrane polymer would cover a layer of $CO_2$ indicator material which would cover a layer of material having a high affinity for $CO_2$. $CO_2$ gas would penetrate the selective membrane polymer and pass through the indicator material layer on its way to the high $CO_2$ affinity layer. In this way the color change of the indicator layer would be transitory and result in a more rapid system response. Materials which have a high affinity for $CO_2$ include, but are not limited to, calcium oxide (CaO), lithium, hydroxide (LiOH), alkali carbonates, ethanolamine and the like. See Kirk-Othmer, *Concise Encyclopedia of Chemical Technology*, Wiley-Interscience, N.Y. (1985), page 213.

Where ethanolamine is used to absorb $CO_2$, it may be adsorbed upon or entrapped within a solid phase support.

The presence of liquid in proximity to detector 38 may decrease its effectiveness. To alleviate this potential difficulty, a drying agent or desiccant may be used to absorb any liquid present in the breathing circuit. To avoid condensation of liquid on the indicator material 68, a desiccant may be either added to the indicator material 68 or placed between indicator material 68 and the membrane 70. Such desiccants may include any of those known to those skilled in the art, for example, calcium sulfate, calcium chloride, magnesium sulfate, molecular sieves, sodium sulfate, calcium oxide, alumina, silica gel or potassium carbonate. See Gordon, A. J., et al., *The Chemist's Companion,* Wiley Interscience, N.Y., 1972, pp. 446-447. The desiccant may either produce a chemical reaction to form a new compound (for example, $Ca(OH)_2$ from CaO) or form a hydrate. Advantageously, the detector may comprise a physical desiccant such as a piece of filter paper placed between indicator material 68 and membrane 70.

In one embodiment of the invention the detector 38 turns purple on inhalation and yellow on exhalation. The speed of response is adequate enough so that even at rapid breathing rates each inhalation and exhalation is indicated. It is of course important that anesthetic gases and agents, oxygen and water vapor do not provide a perceivable response in the material forming the detector 38.

There are a number of possible adaptations which can be made to the invention. For example, the indicator can be shaped to spell "$CO_2$" or "carbon dioxide" so that upon changing from a light color to a dark color it can be immediately recognized by the user that $CO_2$ is in contact with the indicator. Naturally, the device may also be used in a device for intubation of the esophagus using the same principles of the endotracheal tube described above, but of course by observing no color change.

Another adaption of the invention is to detect the color change of the detector 38 by means other than visual observation. As is well known, every color corresponds to one or more different wavelengths of light. Thus, the invention is not limited to changes which are detected by observation with the unaided eye. For example, a change in "color" from one wavelength to another, though not detectable by the unaided eye, may be detected by electronic means or an optical detection scheme. The electronic means could be connected to an alarm, a light bulb or the like. Thus, the respiratory gas composition may be continuously monitored without the need for continuous observation of the detector. Similarly, the color change may be detectable only through the use of transformation equipment such as a blacklight. It can be seen that the term "color," as used throughout this disclosure, is not limited to wavelengths which are detectable by the unaided eye.

As mentioned above, one of the key features of the present invention is the ability to respond rapidly which gives it the ability to completely and reversibly change color in response to a change from inhalation to exhalation and back to inhalation. One aspect of the invention is the acceleration of the exchange of $CO_2$ to and from a liquid phase pH sensor. This is accomplished in accordance with the invention by the addition of a phase transport enhancer which may comprise a quaternary ammonium, phosphonium or pyridinim salt mixed with or added to a layer of pH sensitive dye. A detector comprising a pH-sensitive dye and a phase transport enhancer is able to change color with each breath taken by the patient. This ability to quickly change color with each breath allows the anesthesiologist to confirm that the endotracheal tube is properly placed in the trachea and that the patient is exchanging oxygen for carbon dioxide.

The preferred chemical indicator comprises a porous glass support to which a pH sensitive dye, water, and a phase transport enhancer are adsorbed. In addition, the indicator may further comprise a buffer. The support used may be a material such as an aminopropyl controlled pore glass particles. Tetrabutylammonium hydroxide (TBAH) is pH adjusted with 0.01N phosphate buffer and restored with tetrabutylammonium chloride resulting in a 0.22M tetrabutylammonium solution at pH=8.2. 0.20 ml of concentrated cresol red dye solution is added to 2 ml TBAH prepared as above. This solution is pipetted on to the CPG while positioned on a vacuum filtration apparatus. This sample is dried for several hours in air. The resulting granules are sensitive to $CO_2$ gas and turn from purple to yellow upon exposure within a fraction of a second. The color response is completely and rapidly reversible upon exposure to non-$CO_2$ containing gas.

The support material may be any material upon which a dye can be adsorbed or covalently attached. Various porous and non-porous supports may be used as the support including controlled pore glasses, ion exchange resins, celluloses, collagens, polymerics such as polyacrylamides, polymethacrylates, polystyrenes, polylysines, polyurethanes, polyesters, and polysiloxanes. Such supports are well known to those of ordinary skill in the art and may be prepared according to any methods commonly used. The properties of the surface area, ability to adsorb the dye, and lack of a strong hydrophobicity will affect the performance of the indicator and thus, can be selected to improve the indicator function.

The attachment of the dye to the support material may require derivatization. This activation chemistry may include treatment of glass surfaces with silanizing agents as:

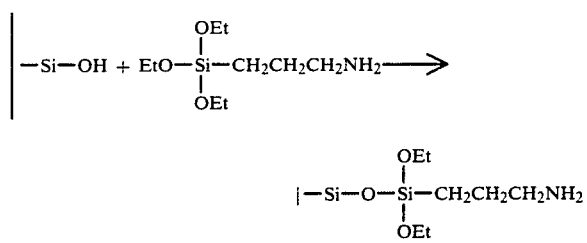

Other silanizing agents may be used, including, but not limited to, those listed in Table 1.

TABLE 1

Silanizing Agents for Derivatization of Glass Surfaces

1. $MeSi(OMe)_3$
2. $VinylSi(OMe)_3$
3. $EtSi(OMe)_3$
4. 5-$HexenylSi(OMe)_3$
5. 2,5,5-$trimethylpentylSi(OMe)_3$
6. $PhSi(OMe)_3$
7. $CH_3C_6H_4Si(OMe)_3$ 8. PhCH$_2$CH$_2$Si(OMe)$_3$
9. BrC$_6$H$_4$Si(OMe)$_3$
10. ClCH$_2$C$_6$H$_4$Si(OMe)$_3$
11. ClCH$_2$CH$_2$CH$_2$Si(OMe)$_3$
12. CF$_3$CH$_2$CH$_2$Si(OMe)$_3$
13. HSCH$_2$CH$_2$CH$_2$Si(OMe)$_3$
14. CH$_2$=C(CH$_3$)COOCH$_2$CH$_2$CH$_2$Si(OMe)$_3$ 15. 

16. MeO[VinylSi(OMe)O]$_2$Me
17. H$_2$NCH$_2$CH$_2$NHCH$_2$CH$_2$CH$_2$Si(OMe)$_3$ Surface derivatization may require further activation prior to dye bonding such as formation of a carbonyl functionality as shown below:

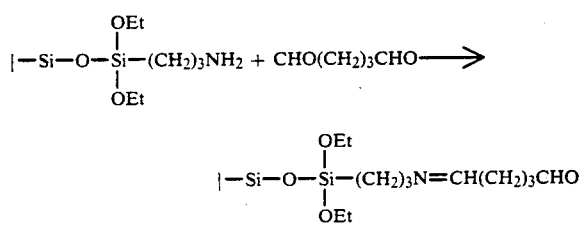

Three examples of derivatization of glass surfaces without use of silanes are as follows:

A. Cyanogen bromide treatment:

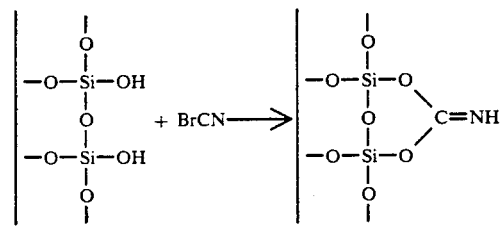

B. Bifunctional bis-diazotized reagent:

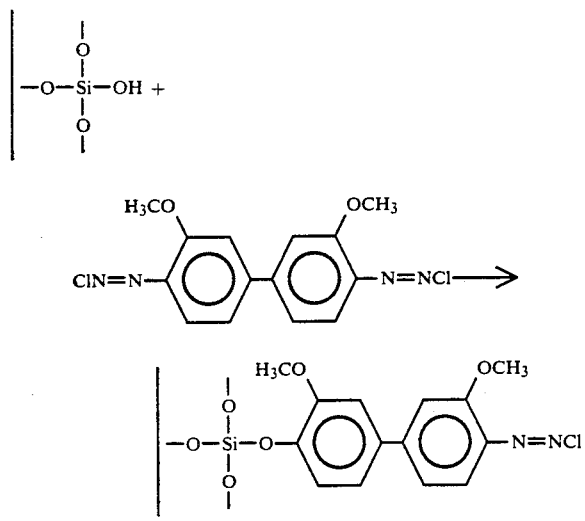

C. Plasma deposition

Activated surfaces may also be prepared by plasma deposition. For example, Furukawa, T., et al., *SIA, Surf. Interface Anal.* 4:204-244 (1982) discloses methods for forming a layer of aluminum oxide by plasma deposition followed by absorption of aminophenyltrimethoxysilane. See also U.S. Pat. application, Ser. No. 707,912, filed Feb. 11, 1977 (available from the NTIS), which discloses plasma polymer deposition to give a polyallylamine surface coating.

Other coupling chemistries include those shown in Table 2. It should be noted that this is only a partial listing and it is anticipated that other chemistries may also be used.

TABLE 2

Activation Chemistries for Derivitized Surfaces

1. Alkylamine surface + Isothiocyanate
2. Alkylamine surface + Carbodiimide
3. Alkylamine surface + triazine trichloride
4. Alkylamine surface + p-nitrobenzoyl chloride
5. Arylamine surface + NaNO$_2$/HCl→Azo coupling
6. Arylamine surface + NaNO$_2$/H+→phenylhydrazine
7. Alkylamine surface + succinic anhydride→carboxy derivative
8. Carboxy derivative of #7 + thionylchloride→acid chloride
9. Carboxy derivative of #7 + N-hydroxysuccinimide, N,N'-dicyclohexylcarbodiimide→active ester In another embodiment, the pH sensitive dye, and optionally the quaternary ammonium salt, may be entrapped within a hydrogel polymer. Suitable hydrogel polymers are those which readily absorb CO$_2$ and water. The absorbed water and carbon dioxide react according to the reaction CO$_2$+H$_2$O=H$_2$CO$_3$ thereby providing a source of hydrogen ions to react with the pH sensitive dye. Suitable hydrogel polymers include, but are not limited to, polymers such as polyacrylamide and acrylamidemethylene bisacrylamide copolymer. The polymer may also contain a crosslinking agent having at least two polymerizable double bonds.

Cross-linking agents having at least two polymerizable double bonds include (i) di- or polyvinyl compounds such as divinylbenzyl and divinyltoluene; (ii) di- or poly-esters of unsaturated mono- or polycarboxylic acids with polyols including, for example, di- or triacrylic acid esters of polyols such as ethylene glycol, trimethylol propane, glycerine, or polyoxyethylene glycols; (iii) bisacrylamides such as N,N-methylenebisacrylamide; (iv) carbamyl esters that can be obtained by reacting polyisocyanates with hydroxyl group-containing monomers; (v) di- or polyallyl ethers of polyols; (vi) di- or polyallyl esters of polycarboxylic acids such as diallyl phthalate, diallyl adipate, and the like; (vii) esters of unsaturated mono- or polycarboxylic acids with monoallyl esters of polyols such as acrylic acid ester of polyethylene glycol monoallyl ether; and (viii) di- or triallyl amines.

An optional component of the reaction mixture used to prepare the pH-sensitive dye-entrapped polymer is a free radical initiator. Such an initiator may comprise any conventional polymerization initiator material including, for example, peroxygen compounds such as sodium, potassium and ammonium persulfates, caprylyl peroxide, benzoyl peroxide, hydrogen peroxide, cumene hydroperoxides, tertiary butyl diperphthalate, tertiary butyl perbenzoate, sodium peracetate, sodium percarbonate and the like. Conventional redox initiator systems can also be utilized. Such systems are formed by combining the foregoing peroxygen compounds with reducing agents such as sodium bisulfite, L-ascorbic acid or ferrous salts. If utilized, the initiator material can comprise up to about 5 mole percent based on the total moles of polymerizable monomer present. More preferably the initiator comprises from about 0.001 to 0.5 mole percent based on the total moles of polymerizable monomer in the reaction mixture.

Various other treatments of the support surface may be required to optimize its properties. These include adjustment of the pore size and composition of the support, preconditioning the surface pH with buffers or other solutions, changing the ionic charge, and controlling the ionic strength of the dye and conditioning solutions.

Various dyes are available which change color in response to changes in pH or the presence of $CO_2$. Any dye which changes color in response to a change in local pH, which can be adsorbed to a porous surface such as controlled pore glass particles, and which has a $pK_a$ lower than the pH of a given support surface can be utilized to practice the invention. Table 3, shown below, is a nonexhaustive list of dyes which have the above properties. Combinations of these dyes may also be used to optimize the contrast of the color change to the pH change. One example of such a mixture is the combination of thymol blue and phenolphthalein.

TABLE 3 pH Sensitive Dyes

1. Phenol red
2. Bromothymol blue
3. Bromocresol purple
4. Rosolic acid
5. Phenolphthalein
6. Cresol red
7. Thymol blue
8. m-Nitrophenol
9. Xylenol blue
10. Curcumin
11. m-Cresol purple
12. Cresolphthalein
13. Thymolphthalein
14. Malachite green
15. N,N-Dimethylaniline
16. Bromocresol green The surface of the support material and the environment of the dye and support must have a local pH in the appropriate range for a $CO_2$ detector reaction to occur. Monobasic and dibasic phosphate buffers, McIlvaine buffers, etc., may be used to achieve this condition. The concentration of the buffer must be low enough so that it does not prevent the pH change induced by $CO_2$. Nonbuffering acids and bases such as HCl and NaOH can also be applied.

Phase transport enhancers, which may comprise quaternary ammonium, phosphonium or pyridinium salts, contained as part of the dye solution applied to the support surface, enhance response of the dye to $CO_2$ gas as well as alter the color and visibility of the indicator.

In general, quaternary salts which are useful in the practice of the invention have the formula (I):

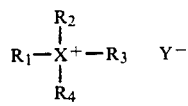

wherein
X = N or P,
$R_1$, $R_2$, $R_3$ and $R_4$ are selected from the group consisting of $C_1$–$C_{12}$ alkyl, triphenylmethyl, phenyl, naphthyl and benzyl,
$C_1$–$C_4$ substituted alkyl wherein the substituent is a $C_1$–$C_4$ alkyl or phenyl group,
$Y^-$ is an anion selected from the group consisting of hydroxide, fluoride, chloride, bromide, iodide, carbonate and tetrafluoroborate.

Other quaternary salts which are useful as phase transport enhancers include pyridinium salts of the formula (II):

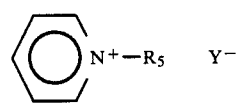

wherein $R_5$ is selected from the group consisting of $C_1$–$C_{12}$ alkyl and benzyl; and Y is an anion selected from the group consisting of hydroxide, fluoride, chloride, bromide, iodide, carbonate, and tetrafluoroborate.

Preferred phase transport enhancers which are useful in the practice of the invention are listed in Table 4.

TABLE 4

Phase Transport Enhancers

1. Tetrabutylammonium hydroxide
2. Tetrabutylammonium chloride
3. Tetraethylammonium bromide
4. Tetraethylammonium p-toluenesulphonate
5. Phenyltrimethylammonium chloride
6. Benzyltrimethylammonium bromide
7. Tetra-n-propylammonium bromide
8. Benzyltriethylammonium tetrafluoroborate
9. n-Dodecyltrimethylammonium bromide
10. Tetraphenylphosphonium chloride
11. n-Hexadecylpyridinium bromide
12. (Triphenylmethyl)triphenyl phosphonium chloride Although the above-detailed description has focused on use in an endotracheal tube, the $CO_2$ indicator disclosed has many other potential uses. For example, the $CO_2$ indicator could be attached to an object to serve as a hand-held life monitor. The object would be held above the mouth or nose of an accident victim to determine whether the victim was breathing.

Along the same lines, the indicator could be mounted in the valve assembly of a manual bag resuscitator. The indicator would help to determine the success of the resuscitation attempt.

An indicator having a high $CO_2$ threshold (e.g., the indicator changes color at $CO_2 > 5\%$) could be used during anesthesia to detect malignant hyperthermia, a disease triggered by anesthetic drugs which leads to a hypermetabolic rate.

The indicator of the present invention could also be used in gas masks to determine if an unconscious worker or soldier was alive without having to remove the mask.

Another possible adaptation of the invention is to quantify the amount of $CO_2$ passing through an endotracheal tube. This can be done by providing a plurality of indicators, each of which respond to different concentrations of $CO_2$. Indicators which respond to different concentrations of $CO_2$ may be prepared by combining the pH-sensitive dye with various buffers which have a pH higher than the $pK_a$ of the buffer. The larger the difference between the pH of the buffer and the $pK_a$ of the pH-sensitive dye, the higher is the concentration of $CO_2$ which is required to cause a reduction in the pH of the support material and, thereby, a change in color. The plurality of indicators may constitute, for example, a series of bands in defined locations on the detector. The bands may be marked, for example, with the percent of atmospheric $CO_2$ which is necessary to cause a color change of the detector.

By selecting a pH-sensitive dye and a phase transport enhancer which give instantaneous color changes in the presence of atmospheric $CO_2$, it is possible to determine the $CO_2$ content of each breath from beginning to end of exhalation in real time. Determination of the $CO_2$ concentration at the end of a breath is important since the gas present at the end of a breath is thought to be in equilibrium with the bloodstream, thus can be a measure of the $pCO_2$ and pH of the blood. A detector comprising a plurality of detectors can be used advantageously to estimate the $pCO_2$ of the blood without withdrawing a blood sample.

As mentioned below, there are a number of different indicator material compositions which may be used to accomplish the goals of the invention. Below are listed a number of examples which yielded varying results.

EXAMPLES

Materials and Methods

Tetrabutylammonium hydroxide was obtained from the Aldrich Chemical Company (Milwaukee, Wis).

EXAMPLE 1

Four silica gel samples were pretreated with a variety of bases to overcome acidic influence on the dye behavior. Previous dye treatments on silica all failed due to acidic effect of the silica on the dye. The four bases comprised 5 M NaOH, 1 M NaOH, 0.05 M phosphate and 15% aqueous tetra t-butylammonium hydroxide (TBAH), a phase transfer catalyst. After presoaking in one of the four bases, the silica gel was then treated with aqueous bromothymol blue. Samples that were treated with NaOH were deep blue and changed color to green-blue after a 50 sec. exposure to 99% $CO_2$. The color change was not reversible. The samples comprising 0.05 M phosphate behaved in the same way but changed color from light green to yellow. The TBAH sample changed from blue to yellow after 50 sec. exposure to 99% $CO_2$, and unlike the other samples, the color reverted to the original blue in the absence of $CO_2$ within approximately 1–2 min. Exposure of these samples to 5% $CO_2$ did not produce a color change.

This was the first observation of unusual dye behavior associated with a quaternary ammonium salt.

EXAMPLE 2

Phenol red was incorporated into five samples of crosslinked acrylamide polymer at various concentrations. The polymer was pulverized then rinsed with phosphate buffer, pH 8.94. Exposure to 99% $CO_2$ produced a color change from red to yellow in 20 sec. The color reverted back to yellow within 4 min. Exposure to 5% $CO_2$ provided a change from red to orange in 2.5 min. The color reverted back to red in the absence of $CO_2$ after many minutes. Addition of $NaHCO_3$ to the indicator material slightly increased response time and slowed recovery time.

EXAMPLE 3

Silica gel was treated with 1 M TBAH, pH 13.10, then soaked in aqueous bromothymol blue. Exposure to 99% $CO_2$ caused the blue silica gel to change to green-yellow within 25 sec. The color reverted back to blue in the absence of $CO_2$ within several minutes. The color contrast was significant; however, the response time was still slow.

EXAMPLE 4

To increase available surface area for dye adsorption, controlled pore glass was utilized. Alkylamine controlled pore glass (CPG) was soaked in 1 M TBAH, pH 9.11, followed by soaking in bromothymol blue. Exposure to 99% $CO_2$ produced a color change from deep blue to medium green within 30 sec. The color immediately but slowly started to revert to deep blue after removal of $CO_2$.

While doing this experiment, a separate sample which had the same pretreatment was treated with bromothymol blue by a pipetting technique (under mild suction) rather than by soaking. This batch displayed rapid, reversible color change from deep blue to midgreen upon exposure to 99%, 5% and respiratory $CO_2$. The forward response time was 5–12 sec. The recovery time was 12–20 sec.

This was the first sample which demonstrated cycling of color at low $CO_2$ concentrations. The pipetting application technique was probably more effective for two reasons: (1) the limitation of dye loading which improves response time, and (2) the prevention of TBAH solution loss caused by soaking in dye solution.

EXAMPLE 5

Bromothymol blue was adsorbed onto 2 CPG samples. A first sample was pretreated with phosphate buffer (pH 6.6). The second sample was untreated. Both samples became deep blue and changed color to blue-green on exposure to 99% $CO_2$. The change was rapid and reversible. Exposure to 5% $CO_2$ produced no color change. This preparation was inferior to the preceding experiment for two reasons: (1) there was little color contrast in the colorimetric response, and (2) there was no sensitivity to low $CO_2$ concentrations.

EXAMPLE 6

The dye cresol red was applied onto amino CPG that had been pretreated with phosphate buffer. Exposure to 99% $CO_2$ produced a color change from purple to red. Although the color change was rapid, the contrast was poor. Exposure to 5% $CO_2$ produced no effect.

EXAMPLE 7

Cresol red was applied to two samples of amino CPG. The first sample was pretreated with 0.1 M phosphate buffer at pH 8.0 to give crimson colored CPG which did not respond to 99% $CO_2$. The second sample was pretreated with 0.5 M TBAH solution, followed by treatment with cresol red, to produce CPG which was deep purple-green. This sample reversibly changed to clear-yellow on exposure to 5% $CO_2$. This sample also responded reversibly to the presence and absence of respiratory $CO_2$.

The unique effect of the TBAH on colorimetric response to $CO_2$ was clearly evident by this experiment.

EXAMPLE 8

Cresol red was applied to three samples having the following pretreatments: (1) 0.5 M TBAH, pH 8.6, 2) 0.4 M NaOH, pH 8.6, and (3) 0.5 M phosphate buffer, pH 8.6. Each sample was then treated with the same cresol red solution, using the same application technique. After drying, sample (1) was purple and changed reversibly and rapidly to yellow upon exposure to 5% $CO_2$. Sample (2) was crimson and changed to yellow upon exposure to 5% $CO_2$. However, the response of sample (2) was not reversible over time. The colorimetric effect disappeared. Sample (3) behaved the same as sample (2).

After one week, only sample (1) continued to change color reversibly to the presence and absence of 5% $CO_2$ and respiratory $CO_2$. The colors showed no apparent deterioration and the response seemed stable and repeatable.

This experiment demonstrates that the reversibility of the samples is due to the presence of TBAH and is not simply a pH or buffering effect.

EXAMPLE 9

An experiment to determine the effect of varying the sequence of dye and TBAH application was performed by loading dye and TBAH solution in reverse order on amino CPG. The samples that received a final layer of TBAH solution produced the best responding material. A one step application of dye combined with TBAH also worked well.

EXAMPLE 10

The dye phenol red was added to a solution of TBAH and pH adjusted to 8.0. Three dye concentrations were prepared. The solutions were then pipetted onto amino CPG. When dry, all samples responded rapidly and reversibly to the presence and absence of 5% $CO_2$. After one week, the response was still active.

The colorimetric range of these samples were purple to yellow. These colors are uncharacteristic of the acid-base spectrum of phenol red. Thus, application of TBAH and cresol red solutions seems to perturb the normal color spectrum associated with this dye.

EXAMPLE 11

The dye xylenol blue was added to TBAH solution and applied to amino CPG to produce a material that changed from turquoise to yellow upon exposure to 5% $CO_2$. This color change was rapid and reversible.

EXAMPLE 12

The dye curcumin was added to a TBAH solution and applied to amino CPG to produce a material that changed color from hot pink to orange yellow upon exposure to 5% $CO_2$. After 8 days, the colors had lost much intensity and response to $CO_2$.

EXAMPLE 13

Sections of glass tubing having controlled pore glass deposited on the interior surface were activated with aminopropyltriethoxysilane. The tubing was then treated with a solution comprising xylenol blue and TBAH, pH 12.0. The samples changed color from blue to yellow reversibly in the presence and absence of $CO_2$, but not as rapidly as did the CPG sample. A disadvantage of this preparation was that the dye was not permanently adsorbed and tended to leach off the CPG upon standing.

EXAMPLE 14

To effect covalent attachment of dye, it was necessary to convert alkylamine CPG to arylamine CPG by reaction first with nitrobenzoyl chloride and then reduction with sodium dithionite. Cresol red was then immobilized to the arylamine surface through a diazo linkage to produce a dark brown CPG at pH 9.0 and orange CPG at pH 3.0. Extensive testing with $CO_2$ produced no color change. The material was then soaked in TBAH. After drying, exposure to 5% $CO_2$ produced a rapid, response remained active for 1 week and then disappeared. Resoaking with TBAH produced a slight response that did not equal original effect.

EXAMPLE 15

Using arylamine glass purchased from Pierce, xylenol blue was attached by a diazo linkage to produce a colorimetric glass that was deep blue in aqueous NaOH and deep red in aqueous HCl. The material did not show response upon exposure to $CO_2$ with or without TBAH treatment.

EXAMPLE 16

The experiment of Example 15 was repeated using the arylamine glass from Pierce to produce a glass that was purple in aqueous NaOH and deep orange in aqueous HCl. The material did not respond upon exposure to $CO_2$, with or without TBAH treatment. This experiment was repeated using bromocresol purple, rosolic acid, xylenol blue and dilute cresol red to produce colorimetric glasses which did not respond to $CO_2$.

EXAMPLE 17

Cresol red was brominated with N-bromosuccinimide and was then coupled to amino glass. The sample was brown in aqueous NaOH and orange in aqueous HCl. Application of TBAH resulted in a color change to forest green which changed to olive green upon exposure to 5% $CO_2$. The color response did not persist.

EXAMPLE 18

Cresol red was covalently coupled to arylamine CPG by a diazo linkage. The sample was deep blue in aqueous NaOH and orange in aqueous HCl, but did not respond upon exposure to $CO_2$, with or without the addition of TBAH solution.

EXAMPLE 19

Phenol red was immobilized by polymerization to amino CPG that had been derivatized with acryloyl chloride to produce a material that was deep crimson in aqueous NaOH and orange in aqueous HCl. The sample did not respond upon exposure to $CO_2$ after treatment with TBAH and pH adjustments.

EXAMPLE 20

Phenol red was immobilized by polymerization to silica gel which was derivatized with methacryloxypropyltrimethoxysilane to produce a glass that was light red in aqueous NaOH and yellow in aqueous HCl. The sample did not respond to $CO_2$ exposure.

EXAMPLE 21

An attempt was made to duplicate the original covalent attachment experiment which was done on derivatized CPG. Alkylamine glass was converted to arylamine glass and then reacted with cresol red to produce a glass that was deep blue in aqueous NaOH and orange in aqueous HCl. Treatment with TBAH, pH 8.5, produced a medium green material which did not respond upon exposure to $CO_2$.

EXAMPLE 22

Phenolphthalein was immobilized to amino CPG that was derivatized with acryloyl chloride to produce a glass that was intensely purple in aqueous NaOH and colorless in aqueous HCl. Exposure to 5% $CO_2$ caused a change from purple to beige which reversed to pale pink in the absence of $CO_2$. The response disappeared after several cycles. Further addition of TBAH did not restore the color response.

EXAMPLE 23

Thymol blue, bromothymol blue and phenophthalein were each adsorbed onto diethylaminoethyl cellulose, an anion exchange resin. The material showed intense colorimetric behavior in solution, but did not response upon exposure to $CO_2$.

EXAMPLE 24

Phenol red and bromothymol blue were each immobilized to amino CPG derivatized with acryloyl chloride. The phenol red glass was magenta in aqueous NaOH and yellow in aqueous HCl. The bromothymol blue glass was green-blue in aqueous NaOH and yellow in aqueous HCl. The samples did not respond to $CO_2$ with or without TBAH.

EXAMPLE 25

The dye Orange I (Tropoelin 000) was coupled to amino CPG by conversion of the sulphonate of Orange I to the sulphonyl chloride followed by treatment with amino CPG to produce a glass that was rust colored in aqueous HCl and deep red in aqueous NaOH. The color contrast was too weak to enable determination of pKa or presence of $CO_2$.

EXAMPLE 26

The dye neutral red was coupled to amino CPG with cyanuric chloride to produce a glass that was brown in aqueous NaOH and red brown in aqueous HCl. The color contrast was too small for use as a detector of $CO_2$.

EXAMPLE 27

Uncoated CPG was derivatized with methacryloxypropyl trimethoxysilane and then reacted with phenol red to produce a glass that was crimson in aqueous NaOH and orange in aqueous HCl. Exposure to 99% $CO_2$ produced a color change from pink to yellow (20 sec.) which reversed to pink in the absence of $CO_2$ within minutes. This indicator material worked only when the material was wet.

EXAMPLE 28

Thymol blue was immobilized to uncoated CPG as described in Example 28 to produce a glass that was orange in aqueous NaOH and scarlet in aqueous HCl. This material did not respond upon exposure to 99% $CO_2$. Addition of TBAH caused a color change to green-yellow. However, the TBAH material did not respond upon exposure to 99% $CO_2$.

EXAMPLE 29

A cresol red glass was prepared by diazo attachment. This material was deep blue in aqueous NaOH. After treatment with TBAH, the sample showed a colorimetric response upon exposure to 99% $CO_2$ which comprised grey-green lightening to a salmon hue. After several cycles, the response faded, but was partially restored by retreatment with TBAH. Eventually $CO_2$ sensitivity disappeared. A third treatment with TBAH produced a material that gave a slight colorimetric response to 99% $CO_2$ but even less response to 5% $CO_2$. This experiment indicated that TBAH could influence covalent attachment and have a restorative effect on colorimetric behavior.

EXAMPLE 30

Since covalent dye attachments were not rendering materials adequately sensitive to $CO_2$ for use as a rapidly responding indicator material, dye adsorption work was resumed. To prevent desorption of the dye, mechanical protection using a membrane was employed.

A concentrated solution of phenol red dissolved in 0.1 M phosphate buffer, pH 9.2, was applied to amino CPG to produce a deep crimson glass that did not respond upon exposure to $CO_2$. A TBAH solution, pH 8.0, was then applied. As sample was drying, the color began to change to the characteristic purple color. When dry, it changed instantly and reversibly to yellow upon exposure to 5% $CO_2$.

The sample was then placed on a glass slide and enclosed with gortex material. The resulting detector responded to 5% $CO_2$ with no loss of color contrast or response time.

EXAMPLE 31

To determine the threshold response to $CO_2$ for various detector samples, dye adsorption onto amino CPG was performed at 4 different pHs, followed by treatment with TBAH at same pH. The sample prepared at the lowest pH, 8.5, responded to 1% $CO_2$. Cresol red samples prepared at pH 9.5, 11.0, and 13.5 all responded, changing purple to yellow with $CO_2$ concentrations as low as 2%. A control sample having no TBAH remained crimson in the presence or absence of $CO_2$. A second control sample, having a combination dye-TBAH one step application, behaved in the same manner as the three test solutions.

Although a quantitative threshold response was not established, it seems that some control over colorimetric effect can be established by controlling the initial pH. An interesting aspect of the TBAH treatment is the remarkable lability of the colorimetric response which can commence at a very basic pH and yet still produce a color response on the acid side of the pKa.

EXAMPLE 32

The previous experiment was repeated using 2x dye concentration to produce samples having more vivid colors. All four pH batches showed slight yellowing upon exposure to 1% $CO_2$. The pH 11.0 sample produced a colorimetric response with best color contrast comprising purple blue to pale yellow.

The normal acid-base range of this cresol red is pH 7.0-8.8. In the presence of TBAH solution, the colorimetric response of this dye is expanded to include 4 pH units.

EXAMPLE 33

Amino CPG was treated with the four pH dye solutions described in Example 32 containing TBAH dissolved in the dye solution. All samples changed color from purple to vivid yellow upon exposure to 2% $CO_2$. The sample showed lightening of color upon exposure to 1% $CO_2$. The response is immediate and recovery is extremely rapid. This one step application is the easiest and has possibly produced the best samples.

EXAMPLE 34

Three different phase transfer catalysts were each combined with a solution of cresol red and applied to amino CPG.

The sample prepared with benzalkonium chloride (pH 8.7) produced a purple glass that changed color to yellow upon exposure to 2% $CO_2$. This response is very similar to those observed with TBAH preparations.

Samples were also prepared containing benzyltrimethylammonium hydroxide at pH 13.0 and 9.0. The pH 13.0 sample changed color from dark purple to grey-yellow upon exposure to 5% $CO_2$. The pH 9.0 sample changed color from mauve to pink yellow upon exposure to 1% $CO_2$.

Samples were also prepared containing tetraethylammonium hydroxide at pH 13.0 and 8.8. The pH 13.0 sample changed color from dark reddish-purple to yellow upon exposure to 10% $CO_2$ and to mauve upon exposure to 5% $CO_2$. The pH 8.8 sample changed color from mauve to yellow-pink upon exposure to 2% $CO_2$.

These experiments indicate the following: (1) that the effect of a phase transfer catalyst on the spectroscopic properties of a dye can be generalized, and (2) that the effect of a phase transfer catalyst in the enhanced mediation of the acid-base colorimetric reaction between a dye and $CO_2$ can be generalized.

The foregoing description of the preferred embodiments of the invention have been presented for purposes of illustration and description. It is not intended to be exhaustive or to limit it to the precise form disclosed. Obviously, many modifications and variations may be made in light of the above teachings.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. Apparatus, comprising:
   means for enabling visual observation of proper placement of an endotracheal tube in the trachea of a patient, said means comprising:
   a. an endotracheal apparatus which indicates a tracheal tube defining a gas path; and
   b. a $CO_2$ detector disposed within said endotracheal apparatus at a location which is in said gas path of said tube and is visible when said endotracheal tube is inserted, said detector comprising a backing and an indicator material, said indicator material comprising a support material, a pH-sensitive dye, and a phase transport enhancer for enhancing a reaction between $H_2CO_3$ and said pH-sensitive dye, said phase transport enhancer having the formula:

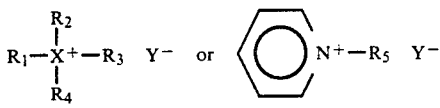

wherein
X = N or P,
$R_1$, $R_2$, $R_3$ and $R_4$ are selected from the group consisting of $C_1$-$C_{12}$ alkyl,
$C_1$-$C_4$ substituted alkyl wherein the substituent is a $C_1$-$C_4$ alkyl or phenyl group,
naphthyl,
benzyl, and
pyridine;
$R_5$ is selected from the group consisting of $C_1$-$C_{12}$ alkyl and benzyl; and
$Y^-$ is an anion selected from the group consisting of hydroxide, fluoride, chloride, bromide, iodide, carbonate and tetrafluoroborate.

2. Apparatus as recited in claim 1, wherein said phase transport enhancer is selected from the group consisting of tetrabutylammonium hydroxide, tetrabutylammonium chloride, tetraethylammonium bromide, tetraethylammonium ammonium, p-toluenesulphonate, phenyltrimethylammonium chloride, benzyltrimethylammonium bromide, tetra-n-propyl-ammonium bromide, benzyltriethylammonium tetrafluoroborate, n-dodecyltrimethylammonium bromide, tetraphenylphosphonium chloride, n-hexadecylpyridinium bromide and triphenylmethyl-triphenylphosphonium chloride.

3. A tracheal intubation apparatus, comprising:
   means for receiving gas expired from a person; and a detector disposed within said means for visually indicating whether a substantial concentration of $CO_2$ is present in said gas, wherein said detector comprises indicator material which changes from one color in the presence of $CO_2$, and changes to another color in response to an absence of $CO_2$, said indicator material comprising a support material, a pH-sensitive dye, and phase transport enhancer for enhancing a reaction between $H_2CO_3$ and said pH-sensitive dye, said phase transport enhancer having the formula:

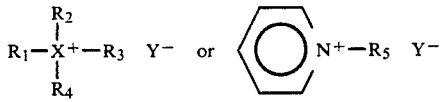

wherein
X = N or P,
$R_1$, $R_2$, $R_3$ and $R_4$ are selected from the group consisting of $C_1$-$C_{12}$ alkyl,
$C_1$-$C_4$ substituted alkyl wherein the substituent is a $C_1$-$C_4$ alkyl or phenyl group, naphthyl,
benzyl, and
pyridine;
$R_5$ is $C_1$-$C_{12}$ alkyl or benzyl; and
$Y^-$ is an anion selected from the group consisting of hydroxide, fluoride, chloride, bromine, iodide, carbonate and tetrafluoroborate.

4. A tracheal intubation apparatus, comprising:
   means for receiving gas expired from a person; and a detector dispersing within said means for visually indicating whether a substantial concentration of $CO_2$ is present in said gas; wherein said detector comprises a phase transport enhancer and a dye solution applied to a support material, said phase transport enhancer enhancing a reaction between $H_2CO_3$ and said dye solution, said phase transport enhancer having the formula:

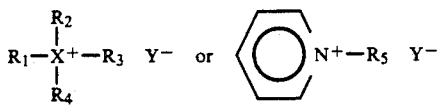

wherein
X = N or P,
$R_1$, $R_2$, $R_3$ and $R_4$ are selected from the group consisting of $C_1$-$C_{12}$ alkyl,
$C_1$-$C_4$ substituted alkyl wherein the substituent is a $C_1$-$C_4$ alkyl or phenyl group,
naphthyl,
benzyl, and
pyridine;
$R_5$ is $C_1$-$C_{12}$ alkyl or benzyl; and
$Y^-$ is an anion selected from the group consisting of hydroxide, fluoride, chloride bromide, iodide, carbonate and tetrafluoroborate.

5. A breath indicator comprising:
 a. means for receiving $CO_2$;
 b. a detector disposed within said means for receiving $CO_2$, said detector comprising means for changing between a first color and a second color, said first color indicating an absence of $CO_2$ and said second color indicating a presence of $CO_2$, said means for changing between a first color and a second color comprising indicator material, said indicator material further comprising a dye and a phase transport enhancer for enhancing a reaction between $HC_2O_3$ and said dye, said phase transport enhancer having the formula:

wherein
X = N or P,
$R_1$, $R_2$, $R_3$ and $R_4$ are selected from the group consisting of $C_1$-$C_{12}$ alkyl,
$C_1$-$C_4$ substituted alkyl wherein the substituent is a $C_1$-$C_4$ alkyl or phenyl group,
naphthyl,
benzyl, and
pyridine;
$R_5$ is $C_1$-$C_{12}$ alkyl or benzyl; and
$Y^-$ is an anion selected from the group consisting of hydroxide, fluoride, chloride, bromide, iodide, carbonate and tetrafluoroborate.

6. A breath indicator comprising:
 a. means for receiving $CO_2$;
 b. a detector disposed within said means for receiving $CO_2$, said detector comprising means for changing between a first color and a second color, said first color indicating an absence of $CO_2$ of said second color indicating a presence of $CO_2$, said means for changing between a first color and a second color comprising indicator material, said indicator material comprising a support material, a pH-sensitive dye applied to said support material, and a phase transport enhancer for enhancing a reaction between $H_2CO_3$ and said pH-sensitive dye, said phase transport enhancer having the formula:

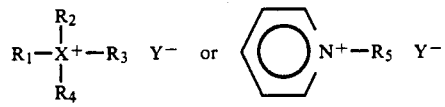

wherein
X = N or P,
$R_1$, $R_2$, $R_3$ and $R_4$ are selected from the group consisting of $C_1$-$C_{12}$ alkyl,
$C_1$-$C_4$ substituted alkyl wherein the substituent is a $C_1$-$C_4$ alkyl or phenyl group,
naphthyl,
benzyl, and
pyridine;
$R_5$ is $C_1$-$C_{12}$ alkyl or benzyl; and
$Y^-$ is an anion selected from the group consisting of hydroxide, fluoride, chloride, bromide, iodide, carbonate and tetrafluoroborate.

7. A method for determining the proper placement of an endotracheal intubation device comprising the steps of
 (1) inserting a device into the trachea of a patient, said method comprising to steps of providing:
  (a) an endotracheal apparatus which includes a tracheal tube defining a gas path; and
  (b) a $CO_2$ detector disposed within said endotracheal apparatus at a location which is in the gas path of said tube and is visible when said endotracheal tube is inserted, said detector being capable of indicating whether a substantial concentration of $CO_2$ is present n said gas, said $CO_2$ detector comprising a backing, and an indicator material, said indicator material comprising a solid phase support, a pH-sensitive dye, and a phase transport enhancer for enhancing a reaction between $H_2CO_3$ and said pH-sensitive dye, said phase transport enhancer having the formula:

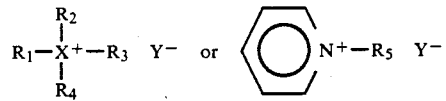

wherein
X = N or P,
$R_1$, $R_2$, $R_3$ and $R_4$ are selected from the group consisting of $C_1$-$C_{12}$ alkyl,
$C_1$-$C_4$ substituted alkyl wherein the substituent is a $C_1$-$C_4$ alkyl or phenyl group,
naphthyl,
benzyl, and
pyridine;
$R_5$ is selected from the group consisting of $C_1$-$C_{12}$ alkyl or benzyl; and
$Y^-$ is an anion selected from the group consisting of hydroxide, fluoride, chloride, bromide, iodide, carbonate and tetrafluoroborate; and (2) observing a color change of the indicator which indicates the presence of $CO_2$ in the respiratory gas and thereby the proper placement of the endotracheal tube.

8. The method of claim 7, wherein said phase transport enhancer is selected from the group consisting of tetrabutylammonium hydroxide, tetrabutylammonium chloride, tetraethylammonium bromide, tetraethylammonium p-toluenesulphonate, phenyltrimethylammonium chloride, benzyltrimethylammonium bromide, tetra-n-propylammonium bromide, benzyltriethylammonium tetrafluoroborate, n-dodecyltrimethylammonium bromide, tetraphenylphosphonium chloride, n-hexadecylpyridinium bromide, and triphenylmethyltriphenylphosphonium chloride.

* * * * *